(12) United States Patent
Giuliani et al.

(10) Patent No.: US 11,273,193 B2
(45) Date of Patent: Mar. 15, 2022

(54) SYNERGISTIC COMPOSITION AS A PROMOTER OF AUTOPHAGY

(71) Applicant: GIULIANI S.P.A., Milan (IT)

(72) Inventors: Giammaria Giuliani, Montagnola (CH); Ralf Paus, Hamburg (DE); Benedetto Grimaldi, Genoa (IT); Barbara Marzani, Carbonara al Ticino (IT); Sergio Baroni, Villa d'Adda (IT)

(73) Assignee: GIULIANI S.P.A., Milan (IT)

( * ) Notice: Subject to any disclaimer, the term of this patent is extended or adjusted under 35 U.S.C. 154(b) by 3 days.

(21) Appl. No.: 16/636,291

(22) PCT Filed: Aug. 2, 2018

(86) PCT No.: PCT/EP2018/071005
§ 371 (c)(1),
(2) Date: Feb. 3, 2020

(87) PCT Pub. No.: WO2019/025548
PCT Pub. Date: Feb. 7, 2019

(65) Prior Publication Data
US 2021/0177925 A1    Jun. 17, 2021

(30) Foreign Application Priority Data
Aug. 3, 2017 (IT) .......................... 102017000089680

(51) Int. Cl.
| | |
|---|---|
| *A61K 36/53* | (2006.01) |
| *A61K 9/00* | (2006.01) |
| *A61K 31/132* | (2006.01) |
| *A61K 31/4188* | (2006.01) |
| *A61K 47/02* | (2006.01) |
| *A61K 47/36* | (2006.01) |

(52) U.S. Cl.
CPC ............ *A61K 36/53* (2013.01); *A61K 9/0014* (2013.01); *A61K 9/0053* (2013.01); *A61K 31/132* (2013.01); *A61K 31/4188* (2013.01); *A61K 47/02* (2013.01); *A61K 47/36* (2013.01); *A61K 2236/15* (2013.01); *A61K 2236/51* (2013.01); *A61K 2236/53* (2013.01)

(58) Field of Classification Search
None
See application file for complete search history.

(56) References Cited

U.S. PATENT DOCUMENTS

| 9,498,429 B2 * | 11/2016 | Giuliani | ................... A61Q 7/00 |
| 2016/0030365 A1 * | 2/2016 | Giuliani | ............... A61K 31/132 |
| | | | 424/93.7 |

FOREIGN PATENT DOCUMENTS

| WO | 2003/063851 A1 | 8/2003 |
| WO | 2014/016407 A1 | 1/2014 |
| WO | 2015/063678 A1 | 5/2015 |

OTHER PUBLICATIONS

Parodi C. et al. Autophagy is Essential for Maintaining the Growth of a Human (Mini)Organ . . . PLoS Biology 1-22, Mar. 28, 2018. (Year: 2018).*
Pinto, D., et al., "Galeopsis Segetum Necker Extracts for the Prevention and Treatment of Hair Loss," Journal of Investigative Dermatology, 136(9):S196 (2016) (abstract).
Ramot, Yuval, et al., "Spermidine Promotes Human Hair Growth and Is a Novel Modulator of Human Epithelial Stem Cell Functions," PloS ONE 6(7):e22564 (2011).
International Search Report and Written Opinion for PCT/EP2018/071005, dated Oct. 29, 2018.
International Preliminary Report on Patentability for PCT/EP2018/071005, dated Nov. 13, 2019.
Parodi et al., "Autophagy is Essential for Maintaining the Growth of a Human (Mini)Organ: Evidence from Scalp Hair Follicle Organ Culture," PloS Biology 16(3):e20022864 (2018).

* cited by examiner

*Primary Examiner* — Ralph J Gitomer
(74) *Attorney, Agent, or Firm* — Troutman Pepper Hamilton Sanders LLP (Rochester)

(57) ABSTRACT

The invention relates to a synergistic composition comprising a dry extract of plant of genus *Galeopsis* and a compound promoting autophagy selected from biotin and R-N1-spermidine or a salt thereof, wherein R is hydrogen or methyl and mixtures thereof. The synergistic compositions according to the invention may be in the form of a topical formulation or oral formulation and is useful as a promoter of autophagy especially in cells of human scalp hair follicles and in promoting hair growth and/or in the treatment of hair thinning or hair loss.

4 Claims, 3 Drawing Sheets

SYNERGISTIC COMPOSITION AS A PROMOTER OF AUTOPHAGY

This application is a national stage application under 35 U.S.C. § 371 of PCT Application No. PCT/EP2018/071005, filed Aug. 2, 2018, which claims the priority benefit of Italian Patent Application No. 102017000089680, filed Aug. 3, 2017.

FIELD OF INVENTION

The invention concerns synergic compositions and their use as a promoter of autophagy in the nutritional, medical or cosmetic fields.

STATE OF THE ART

Autophagy (or autophagocytosis) is the natural, regulated mechanism of the cell that disassembles unnecessary or dysfunctional components. Autophagy allows the orderly degradation and recycling of cellular components. In macroautophagy, targeted cytoplasmic constituents are isolated from the rest of the cell within a double-membraned vesicle known as an autophagosome. The autophagosome eventually fuses with lysosomes and the contents are degraded and recycled. Three forms of autophagy are commonly described: macroautophagy, microautophagy, and chaperone-mediated autophagy (CMA), along with mitophagy. In disease, autophagy has been seen as an adaptive response to stress, which promotes survival, whereas in other cases it appears to promote cell death and morbidity. In the extreme case of starvation, the breakdown of cellular components promotes cellular survival by maintaining cellular energy level. Therefore autophagy plays a crucial role in health, disease and ageing regulating such central cellular processes as adaptive stress responses, differentiation, tissue development and homeostasis.

In Angeleen Fleming et al *"Chemical modulators of autophagy as biological probes and potential therapeutics"*, Nature Chemical Biology 7, 9-17 (2011) the authors demonstrated that autophagy has unexpected pleiotropic functions that favor survival of the cell, including nutrient supply under starvation, cleaning of the cellular interior, defense against infection and antigen presentation. Defective autophagy is hence associated with a diverse range of disease states, including neurodegeneration, cancer and Crohn's disease.

In Teng Yu et al, "Targeting autophagy in skin diseases, J Mol Med (2015) 93:31-38" the mechanisms of autophagy on the pathogenesis of skin diseases is studied and reported. Specifically the role of the autophagy—in autoimmune skin disorders such as psoriasis, systematic lupus erythematosus (SLE) and vitiligo, —infectious skin disorders, —skin cancer disorders such as squamous cell carcinoma and melanoma, is reported.

In order to therapeutically modulate autophagy for investigating suppressors and inducers of autophagy human organ models were studied.

In Tobias Eiserberg et al, *"Induction of autophagy by spermidine promotes longevity"* Nature cell biology, volume 11, number 11, November 2009, the effects of spermidine, a natural polyamine, were studied in yeast, flies and worms. The authors reported that the administration of spermidine extended the life of them. Furthermore, spermidine administration potentially inhibited oxidative stress in ageing mice. It was demonstrated that autophagy constituted the major lysosomal degradation pathway for recycling damaged and potentially harmful cellular material.

The inventors realized that as a complete, cyclically remodeled (mini)organs, the organ culture of human scalp hair follicles (HFs) may provide such a model since such follicles, after massive growth activity (anagen) spontaneously enter into apoptosis-driven organ involution (catagen). As it is known, the life cycle of the hair bulb of the follicle is essentially represented by three subsequent phases: anagen (growth), catagen (involution) and telogen (rest phase).

Surprisingly, the inventors found out that the life cycle of the hair follicle can be modulated by the autophagy mechanism and on the basis of the model of human scalp hair follicle promoting agents were investigating.

In view of the study the inventors hypothesized that late-stage anagen scalp HFs, whose hair matrix hepitelium proliferates at a high rate than most malignant tumors and it is exposed to a number of stressors, are likely to come under increasing pressure to maintain tissue homeostasis and may require a substantial autophagy flux to their flux to maintain their growth.

As it is known different stressors negatively affect the life cycle of the hair follicle, thus determining a reduction of the number of hair and their thinning.

Therefore an object of the present invention is to provide a composition suitable as a promoter of autophagy in cells of human scalp hair follicles.

Another object hence is to provide a composition for promoting hair growth and/or inhibiting or delaying hair loss in the human scalp.

Another object is the provision of a composition for the treatment of conditions mediated by autophagy.

SUMMARY OF THE INVENTION

Starting from studying the organ culture of human scalp hair follicles (HFs), the inventors found out a combination of compounds inducing autophagy in the studied model and showing a synergistic effect in promoting autophagy especially in cells of human scalp, hair follicles.

After investigation, the composition having a synergistic effect was unexpectedly an extract of plant of genus *Galeopsis* combined with a further compound promoting autophagy, especially in cells of human scalp selected from R—$N^1$-spermidine or its salt, biotin and a mixture thereof.

Therefore, the above objects have been achieved by a synergistic composition comprising an extract of plant of genus *Galeopsis* and R—$N^1$-spermidine or a salt thereof, wherein R is hydrogen or methyl.

Alternatively, the above objects have been achieved by a synergistic composition comprising an extract of plant of genus *Galeopsis* and biotin.

In a further alternative embodiment, the above objects have been achieved by a synergistic composition comprising an extract of plant of genus *Galeopsis*, biotin and R—$N^1$-spermidine or a salt thereof, wherein R is hydrogen.

Preferably and surprisingly, the inventors observed that the administration of the above compositions, either by the topical or oral route of administration, promoted in a synergistic way the autophagy in cells especially of hair follicles, in a subject suffering from hair thinning, thus determining a progressive thickening of the suffered areas of the scalp.

In accordance to a further aspect, the present invention hence provides for the use of the above compositions for stimulating the physiological growth of the hair.

In accordance to a still further aspect the present invention hence provides the above compositions for use in the treatment or in the prevention of hair loss or of a scalp disease.

DETAILED DESCRIPTION OF THE INVENTION

Figure 1:
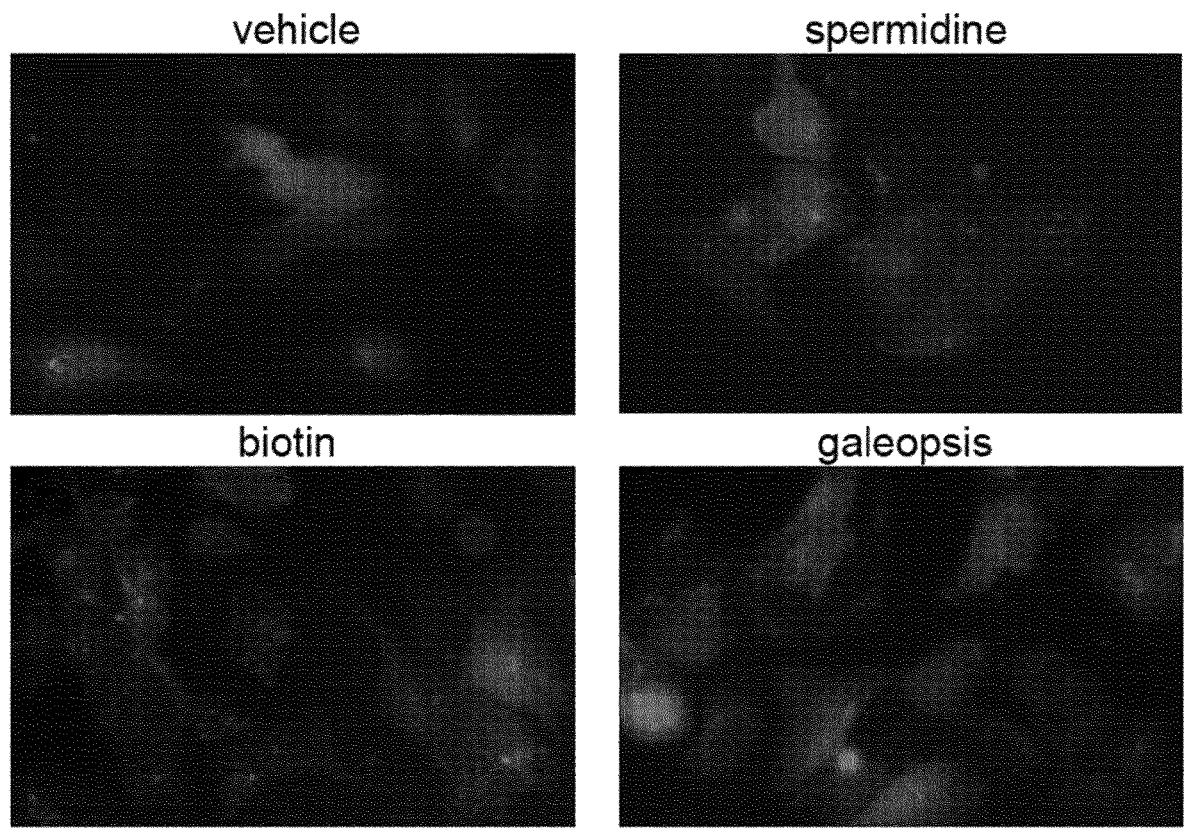
FIG. 1 shows representative images of U2OS cells transduced with a construct expressing the autophagic protein LC3 fused with a Red Fluorescent Protein (RFP) treated 6 hours with the indicated substances. The previously characterized autophagy inducer, spermidine, was used as positive reference.

The invention hence concerns a synergistic composition as defined in claim 1. In a preferred and advantageous embodiment the invention relates to a synergistic composition of an extract of plant of genus *Galeopsis*, R—N$^1$-spermidine or a salt thereof, wherein R is hydrogen or methyl, and biotin.

The extract of the composition of the above compositions origins from a plant belonging to the genus *Galeopsis*.

In an embodiment the extract of *Galeopsis* is a dry extract in particular of the species *Galeopsis segetum*, commonly known as Downy Hemp-nettle, i.e. a species of flowering plant in the sage family, Lamiaceae.

In another embodiment, the extract of *Galeopsis* is an extract in particular of the species *Galeopsis* tetrahit.

In certain embodiments, the plant extract is a mixture of extracts from *Galeopsis segetum* and *Galeopsis* tetrahit.

The extract of the invention is obtained by extraction from a part of the plant, such as roots, leaves, fruits and flowers, preferably the aerial parts of the plant.

According to some embodiments, the plant extract of the invention is obtained by extraction from a part of the plant or from a tissue thereof using a physiologically acceptable solvent as the extraction medium.

With the term of "physiologically acceptable solvent", it is meant a solvent that does not produce significant adverse reactions when introduced into the human body or applied to the human organism. Typically, with the term solvent is meant the solvent used for extracting the biologically active components from a portion of plant of *Galeopsis*.

A suitable solvent to obtain the plant extract is a physiologically acceptable liquid in which at least some of the biologically active components of the selected plant are soluble and in which they do not undergo an alteration that deprives them of activity.

The preferred morphological parts of the plant used for carrying out the extraction is the shoot system which includes stems, leaves, blossom and flowers.

The solvent used for carrying out the extraction may be a physiologically acceptable solvent. Suitable solvents may be nonpolar solvents such as diethyl ether, chloroform, polar aprotic solvents such as ethyl acetate, dichloroethane and polar protic solvents such as $C_1$-$C_6$ alcohols and aqueous solutions containing them. The use of polar protic solvents is preferred. Typical polar protic solvents include water, ethanol, propanol, isopropyl alcohol and mixtures thereof. Preferred solvents are water ethyl alcohol and a mixture thereof.

In certain embodiments, after the extraction with a polar protic solvent, preferably ethanol, the extract is preferably filtered, concentrated and clarified. The obtained extract is then preferably purified. The purification is more preferably carried out by eluting in column with a solvent. The solvent can be for example water or ethanol. The purified extract is then preferably concentrated and dried. The dry extract so obtained can be optionally ground and optionally added with excipients to yield the final dry extract to be used in the inventive compositions. The optional excipients comprised in the dry extract are preferably selected from the group consisting of maltodextrin and colloidal anhydrous silica gel.

To obtain the plant extract of *Galeopsis tetrahit*, solid-liquid extraction techniques may be used to separate/extract one or more biologically active components from the plant's vegetable tissues.

In certain embodiments, the extraction of one or more biologically active components takes place by macerating a *Galeopsis tetrahit* vegetable portion or matrix in a suitable solvent as referred above.

For example, a suitable extract can be obtained by dipping or macerating a portion of aerial parts of *Galeopsis* in a water-ethanol mixture, for a time suitable for enriching the solvent of one or more biologically active components contained in the plant portion. Under these conditions, the extraction of the biologically active components from the plant tissues of the selected plant takes place, substantially, by diffusion and/or osmosis. The maceration time of the plant portions in the solvent is variable, for example from 1 to 48 hours.

In accordance to certain embodiments the dry extract of the *Galeopsis* is obtainable by the following steps:
grinding at least one part of the plant *Galeopsis*;
extracting with a solvent, preferably a physiologically acceptable solvent;
filtering the extract;
purifying the filtered extract, preferably by eluting in a column with a solvent;
drying the purified extract;
grinding the dried purified extract.

In some embodiments, the extraction step can be repeated two or three times. When the solvent is removed, for example by evaporation, a solid support or excipient may optionally be added, such as, by way of non-limiting example, starches or maltodextrins, to obtain the extract in the form of dry powder.

Typically, the extract obtained from *Galeopsis Tetrahit* or *segetum*, can be fluid, soft or dry and preferably is dry.

For example:
in the fluid extract, 1 ml of extract contains biologically active components soluble in 1 g of vegetable drug;
in the soft extract, the solvent is partially evaporated in particular until the extract not wets a filter paper;
in the dry extract, the solvent is evaporated almost completely to obtain a powder.

It is possible to prepare extracts of *Galeopsis* of different polarity.

For example, it is possible to obtain a high polarity extract using a polar solvent such as a hydroalcoholic solution, an intermediate polarity extract using a less polar solvent such as ethylacetate or an apolar extract using supercritical $CO_2$ with which it is possible to extract fractions of active phyto-complexes.

In certain embodiments, the extraction is carried out using a weight ratio between solvent and vegetable matrix ranging from 1:10 to 10:1.

It is possible to extract the biologically active plant components from the *Galeopsis* plant by using alternative extraction techniques such as, for example, by digestion, infusion, squeezing, decoction, percolation, counter-current extraction, soxhlet, extraction with supercritical gases or ultrasounds.

In addition to the plant extract, the synergistic composition may comprise R—$N^1$-spermidine or its salt, wherein R is hydrogen or methyl. Spermidine is a polyamine, having IUPAC name N'-(3-aminopropyl)butane-1,4-diamine. Spermidine can be present in the composition in the form of a salt, preferably a pharmaceutically acceptable salt, more preferably in the form of trihydrochloride.

In addition to the plant extract, the synergistic composition may comprise Biotin, a water-soluble B-vitamin, also called vitamin B7 and formerly known as vitamin H or coenzyme R.

Biotin is composed of a ureido ring fused with a tetrahydrothiophene ring having IUPAC name 5-[(3aS,4S,6aR)-2-oxohexahydro-1H-thieno[3,4-d]imidazole-4-yl]pentanoic acid (CAS number 58-85-5).

The inventors revealed for the first time the property of biotin of being a promoter of autophagy in human cells, specifically cells of human scalp hair follicles.

Therefore the invention also relates to biotin or a composition containing biotin according to any one of the embodiments described above, for cosmetic or nutraceutical or medical use as a promoter of autophagy in the treatment of diseases modulated by autophagy.

Diseases modulated by autophagy are for example selected from the group consisting of neurodegeneration, cancer, Crohn's disease and skin diseases. Specifically among the skin diseases, autoimmune skin disorders such as psoriasis, systematic lupus erythematosus (SLE) and vitiligo, —infectious skin disorders, —skin cancer disorders such as squamous cell carcinoma and melanoma, can be cited.

For the first time the extract of genus *Galeopsis*, preferably of the species *Galeopsis segetum* and *Galeopsis tetrahit* is used as a promoter of autophagy in the treatment of skin diseases.

Preferably and surprisingly, the inventors observed that the administration of the above compositions, typically either by the topical or oral route of administration, promoted in a synergistic way the autophagy in cells of human scalp hair follicles in a subject suffering from hair thinning, thus determining a progressive thickening of the suffered areas of the scalp.

Typically, the composition of the invention comprises a physiologically and/or pharmaceutically acceptable carrier, diluent or excipient.

The physiologically or pharmaceutically suitable carrier, diluent or excipient may be selected based on the route of administration for which the resulting pharmaceutical composition is intended. Any carrier and/or excipient suitable for the desired preparation form for administration is contemplated in the uses of the plant extract or active ingredients therein described therein.

Within the scope of the present invention, the term "carrier" refers to an excipient, vehicle, diluent or adjuvant, which may or may be present in the composition of the invention.

The composition of the invention can be formulated in a form for topical application or in a form for oral administration.

In some embodiments, the composition is for the topical application. In this application, the composition of the invention can be applied, in an effective quantity, directly on the scalp or skin of a human beings.

For example, in the treatment of hair loss or thinning forms a cosmetically/physiologically active amount of composition can be applied directly on the scalp, once or more times a day conveniently for cycles lasting 2-3 months, alternated with periods of absence of treatment.

According to these aspects, the invention also relates to a cosmetic treatment method comprising the application on the scalp, or portion thereof, of an effective quantity of a composition according to one or more of the embodiments described and/or claimed therein.

The amount of the dry extract of *Galeopsis*, preferably in the form of species *Galeopsis segetum* or *Galeopsis tetrahit*, in the topical formulation of the compositions of the invention is in the range of 0.0003% to 0.01% weight by weight with respect to the total weight of the formulation.

The amount of biotin in the topical formulation of the compositions of the invention is in the range of 0.0006% to 0.075% weight by weight with respect to the total weight of the formulation.

In the topical form, the composition comprises preferably $N^1$-methylspermidine. In the topical form, $N^1$-metil spermidine or spermidine is preferably comprised in the range of 0.0005-0.1% weight by weight with respect to the total weight of the formulation.

Among the commonly excipients in the topical formulation for cosmetic use or for pharmaceutical use preservatives, bacterial agents, emulsifying agents, buffers, lubrificants, wetting agents, conditioning agents and colouring agents can be cited. The composition for topical application may be in solid, semisolid or fluid form. Suitable formulations in solid form include creams, gels, ointments, pastes, unguents.

In other embodiments, the formulation for local administration is in fluid form, for example in the form of lotions, gels, shampoos, suspensions, emulsions.

In the case of fluid or semi-fluid formulations form, the plant extract can be diluted in a carrier in physiologically acceptable liquid form such as water, alcohol, hydroalcoholic or glyceric solution or mixed with other liquids suitable for local application.

By way of example, the compositions of the invention in liquid form can be prepared by dissolving the components in water and/or alcohol. The liquid composition can be buffered to reach a pH range conveniently selected from 5 to 7 to be compatible with the pH of the scalp and then filtered and packaged in suitable containers such as bottles or vials.

In some embodiments, the compositions of the invention may comprise excipients commonly used in the formulation of cosmetic or pharmaceutical preparations for local use, such as preservatives, bactericidal agents, stabilizers, emulsifiers, buffers, wetting, dyes and other excipients commonly used in preparation techniques.

In one embodiment, the formulation for the local application is in the form of an emulsion containing the extract carried in a suitable excipient. In some embodiments, the composition for topical application comprises an excipient of the hydroxymethylcellulose type and/or gelling with HLB suitable for the formulation and the substances.

According to other embodiments, the composition of the invention is in form for oral administration. In these cases, the composition contains the components as previously defined and one or more vehicles or excipients suitable for oral administration.

The amount of the extract of *Galeopsis*, preferably in the form of species *Galeopsis segetum* or *Galeopsis tetrahit*, in the oral formulation of the compositions of the invention is in the range of 0.1 mg to 20 mg per single dose.

The amount of biotin in the oral formulation of the compositions of the invention is in the range of 0.03 mg to 0.08 mg per single dose.

In the oral form, the composition comprises preferably spermidine or a salt thereof, more preferably spermidine is in the form of a salt.

In the oral form, $N^1$-methylspermidine (or its salt), or spermidine (or its salt) is preferably comprised in the range of 0.3 mg to 0.8 mg per single dose.

By way of example, suitable excipients for oral administration include cellulose derivatives such as hydroxymethylcellulose, hydroxypropyl methylcellulose, methylcellulose, hydroxypropyl cellulose, hydroxyethyl cellulose, carboxyethyl cellulose, ethylhydroxyethyl cellulose, cellulose acetate butyrate, cellulose acetate phthalate, and mixtures thereof.

Further examples of suitable excipients include the polymers belonging to the lactam family such as pyrrolidone and its derivatives, for example polyvinylpyrrolidone, polyvinylpolypyrrolidone and their mixtures, inorganic salts such as calcium or dicalcium phosphate, lubricants such as magnesium stearate, triacylglycerols and mixtures thereof.

The compositions for oral administration may be in solid or liquid form. Typical solid form compositions include tablets, capsules, powders, granules, pills. Examples of compositions in liquid form include solutions, emulsions, suspensions, syrups. The compositions may also be in the controlled release form of the active components contained therein.

The tablets generally comprise a suitable carrier or excipient in which the plant extract is dispersed, typically in dry form.

Among the typical excipients or carriers for oral administration disintegrating agents, fillers, preservatives can be included in the formulation of the composition. In certain embodiments, the composition of the invention is a nutritional product, a dietetic product or a nutraceutical product.

The term nutritional supplement means a product, which improves the nutritional status and may be used to support or improve the functional activity of one or more organs or the functionality of the human body within the physiological boundaries. The compositions of the invention being autophagy promoters are hence hair-growth promoting nutraceuticals and cosmeceuticals.

In accordance to a further aspect, the present invention hence provides for the use of the synergistic above cited compositions for stimulating the physiological growth of the hair and/or for the treatment of hair loss.

In accordance to a further specific aspect, the present invention hence provides for the use of the topical or oral formulation comprising the above cited compositions for stimulating the physiological growth of the hair.

In accordance to a still further aspect the present invention hence provides for the above cited synergistic compositions for use a promoter of autophagy in cells of human scalp hair follicles in the treatment and in the prevention of hair loss and for stimulating hair growth.

In accordance to a further specific aspect, the present invention hence provides for the use of the topical or oral formulation comprising the above compositions for stimulating the hair growth or for the treatment or prevention of hair loss.

The link between the promotion of autophagy and the above mentioned activities of the compositions of the invention are proven by the tests described in the following Example 13. In particular, the scientific article to Chiara Parodi et al.: "Autophagy is essential for maintaining the growth of a human (mini)organ: Evidence from scalp hair follicle organ culture" published on *PLOS* Biology vol. 16(3), 2018, 28, Mar.: 10.1371/journal.pbio.2002864 shows that the test carried out on human bone osteosarcoma epithelial cells is an established model for proving the efficacy of the composition on the stimulation of hair growth.

The experimental show the synergism in the stimulation of autophagy in a validated in vitro model. The data and publication show that autophagy is essential for the growth of hair follicle. The composition of the invention stimulates autophagy and consequently is effective in stimulating hair growth.

In certain aspects the invention provides the above composition for use in the treatment of a disorders in the hair growth such as in the case of alopecia androgenetica or defluvium.

In a further aspect the invention provides for the use of the above compositions as a promoter of autophagy in the treatment of a skin disorder.

The inventors found out also that a composition comprising N-methylspermidine and biotin was suitable as a promoter of autophagy in the treatment of skin diseases.

The amounts administered and the frequency of administration of the composition will depend on the type and severity of the diseases to be treated.

The invention will be now detailed by reference to specific embodiments showing the synergistic results achieved by the compositions of the invention and should not be considered limitative. The amounts of the components indicated are expressed as percentages (%) weight by weight (w/w) or in mg per single dose of administration.

EXPERIMENTAL PARTS

Example 1

Preparation of the Extract of *Galeopsis* Segetum

The preparation of *Galeopsis segetum* dry extract was performed by extraction with Ethanol 40% followed by column purification. The steps are described in the following paragraphs.

Extraction

Ground desiccated aerial parts of *G. segetum* were extracted twice at 50° C. for 2 hours with 40% ethanol. Solid and liquid were separated by a dekanter.

The leachates were filtered, concentrated under vacuum and then clarified by centrifugation.

Purification

A column was filled with ion exchange XAD7HP sorbent resin which was previously soaked in 95% Ethanol and maintained in contact for 10 hours. The packed column was then washed with water continuing until the conductivity of the eluate reached the same value of the loaded water.

The purification of the extract was made on the XAD7HP packed column eluting initially with water and then with 70% Ethanol.

The collected eluates were concentrated under vacuum.

Ethanol was added to the concentrated solution and then the solution was heated at 70-75° C. for 30 minutes in order to reduce the bioburden level.

The solution was again concentrated under vacuum, dried at 50° C. for 24 hours and then ground and mixed with excipients (maltodextrin and colloidal anhydrous silica gel 90/10) to yield the final product.

Example 2

Preparation of the Extract of Galeopsis Tetrahit

The preparation of Galeopsis tetrahit dry extract was performed following exactly the same procedure described at the previous paragraphs for the extraction of Galeopsis segetum.

Example 3

Revitalizing Shampoo

| Ingredients | % w/w |
| --- | --- |
| Zetesol MGS/B | 16-49 |
| Sodium Lauroyl Sarcosinate | 4-12 |
| Mirasheen CP 820/G | 2-6 |
| Rewoderm LI S 80 | 1-4 |
| Euxyl K 701 | 1-2 |
| BC 2262 | 0.5-1.4 |
| Cocamide MIPA | 0.5-1.4 |
| Potassium Undecylenoyl Hydrolyzed Wheat protein | 0.5-1.4 |
| Ccitric acid monohydrate | 0.4-1.2 |
| Betaine monohydrate | 0.2-0.7 |
| Lauryl methyl gluceth-10 hydroxypropyldimonium chloride | 0.2-0.7 |
| Gafquat 755 N-O | 0.2-0.5 |
| D-Panthenol | 0.1-0.3 |
| Trisodium ethylenediamine disuccinate | 0.1-0.3 |
| BHA | 0.01-0.02 |
| Hydroxypropyltrimonium hyaluronate | 0.01-0.02 |
| Galeopsis segetum dry extract | 0.003-0.009 |
| Biotin | 0.001-0.03 |
| Meditanox H-10 | 0.0005-0.0015 |
| $N^1$-Methylspermidine | 0.0005-0.1 |
| Lecithin | 0.0004-0.0011 |
| Fomblin HC/PU-CAT5 | 0.0002-0.0005 |
| Water to 100 mL | |

Example N. 4

Reinforcing Shampoo

| Ingredients | % w/w |
| --- | --- |
| Zetesol MGS/B | 15-50 |
| Sodium N-lauroyl sarcosinate | 4-12 |
| Mirasheen CP 820/G | 2-6 |
| Rewoderm LI S 80 | 1-4 |
| Euxyl K 701 | 1-2 |
| Cocamide MIPA | 0.5-1.4 |
| Potassium Undecylenoyl Hydrolyzed Wheat protein | 0.5-1.4 |
| Ccitric acid monohydrate | 0.4-1.1 |
| BC 2262 | 0.3-0.8 |
| Betaine monohydrate | 0.2-0.7 |
| Lauryl methyl gluceth-10 hydroxypropyldimonium chloride | 0.2-0.7 |
| Abil Soft AF 100 | 0.2-0.6 |
| Gafquat 755 N-0 | 0.2-0.5 |
| D-Panthenol | 0.1-0.3 |
| Trisodium ethylenediamine disuccinate | 0.1-0.3 |
| BHA | 0.01-0.02 |
| Hydroxypropyltrimonium hyaluronate | 0.01-0.02 |
| Galeopsis segetum dry extract | 0.003-0.009 |
| Biotin | 0.001-0.003 |
| Meditanox H-10 | 0.001-0.002 |
| $N^1$-Methylspermidine | 0.001-0.002 |
| Lecithin NAT 8539 | 0.0004-0.0011 |
| Fomblin HC/PU-CAT5 | 0.0002-0.0005 |
| Water to 100 mL | |

Example N. 5

Lotion

| Ingredients | % w/w |
| --- | --- |
| Ethanol | 9-27 |
| Calcium Pantothenate | 1-2 |
| PEG-40 Hydrogenated castor oil | 1-2 |
| Lactic acid sol. 80% | 0.1-0.4 |
| Lypobelle soyaglycone | 0.04-0.13 |
| Hydroxypropyltrimonium hyaluronate | 0.03-0.1 |
| $N^1$-methylspermidine | 0.03-0.09 |
| Lecithin NAT 8539 | 0.02-0.07 |
| Octadecyl di-t-butyl-4-hydroxyhydrocinnamate | 0.02-0.07 |
| Fomblin HC/PU-CAT5 | 0.009-0.027 |
| Biotin | 0.007-0.022 |
| Meditanox H-10 | 0.0005-0.0015 |
| Water to 100 mL | |

Example N. 6

Fortifying Conditioner

| Ingredients | % w/w |
| --- | --- |
| Cetyl trimethyl ammonium chloride | 3-9 |
| Cetyl stearyl alcohol | 3-8 |
| Silsoft 8812 | 2-7 |
| Arlacel 165-PA-(MV) | 2-5 |
| Glyceryl stearate | 2-5 |
| C12-13 alkyl lactate | 1-3 |
| Dow Corning CE 8401 | 1-2 |
| Xylitol | 1-2 |
| Biocontrol synergy BAS | 0.3-0.9 |
| Hydroxyethylcellulose | 0.3-0.9 |
| D-Panthenol | 0.3-0.8 |
| Uniglucan G-51 | 0.3-0.8 |
| Liquid lactic acid | 0.1-0.4 |
| Phytantriol | 0.1-0.3 |
| Sodium benzoate | 0.1-0.3 |
| Sodium dehydroacetate | 0.1-0.3 |
| Cyclopentasiloxane | 0.1-0.2 |
| Disodium EDTA dihydrate | 0.1-0.2 |
| Sericin | 0.1-0.2 |
| Hydroxypropyltrimonium hyaluronate | 0.01-0.02 |
| Galeopsis segetum dry extract | 0-0.01 |
| Biotin | 0.01-0.03 |
| Meditanox H-10 | 0.001-0.002 |
| Lecithin NAT 8539 | 0.0004-0.0011 |
| Fomblin HC/PU-CAT5 | 0.0002-0.0005 |
| $N^1$-methylspermidine | 0.025-0.075 |
| Water to 100 mL | |

Example N. 7

Fortifying Conditioner

| Ingredients | % w/w |
|---|---|
| Cetostearilic alcohol | 4-11 |
| Cetyl trimethyl ammonium chloride | 3-8 |
| Aquacat PF618 Clear Cationic Solution | 2-6 |
| 1,2 Propandiol | 2-5 |
| SI-TEC AME 6057 | 1-3 |
| Incroquat behenyl TMS | 1-2 |
| D-Panthenol | 0.4-1.2 |
| phenoxyethanol | 0.4-1.2 |
| Glyceryl stearate | 0.4-1.2 |
| Mycomplex | 0.4-1.2 |
| Ceraphyl 60 | 0.3-0.8 |
| Collasurge - LQ- (WD) | 0.3-0.8 |
| Safflower oil | 0.2-0.5 |
| Amipearl intense silver1161 | 0.1-0.3 |
| Tocopheryl acetate | 0.1-0.3 |
| Hydroxyethylcellulose | 0.1-0.3 |
| Uvinul A plus B | 0.1-0.2 |
| Cyclopentasiloxane | 0.1-0.2 |
| Dekaben BL | 0.1-0.2 |
| Disodium EDTA dihydrate | 0.1-0.2 |
| Rewoteric AM 2C NM | 0.1-0.2 |
| citric acid monohydrate | 0.03-0.08 |
| Butylatedhydroxytoluene | 0.03-0.08 |
| Calcium Pantothenate | 0.01-0.03 |
| Hydroxypropyltrimonium hyaluronate | 0.01-0.02 |
| Biotin | 0.001-0.02 |
| SK-Influx V | 0.001-0.003 |
| Rutin | 0.0006-0.0017 |
| Galeopsis tetrahit dry extract | 0.001-0.002 |
| Meditanox H-10 | 0.0005-0.0015 |
| Vitis vinifera seeds dry extract | 0.0005-0.0015 |
| Lecithin NAT 8539 | 0.0004-0.0012 |
| Zeaxantina Sol. 20% oil | 0.0002-0.0006 |
| Fomblin HC/PU-CAT5 | 0.0002-0.0005 |
| $N^1$-methylspermidine | 0.0045-0.0135 |
| Water to 100 mL | |

Example N. 8

Fortifying Gel

| Ingredients (INCI) | % w/w |
|---|---|
| Fixate PLUS Polymer | 2-5 |
| PEG-40 Hydrogenated castor oil | 1-3 |
| Perfume Apollon 436/F 0505436F | 1-2 |
| Not crystallizing Sorbitol 70% | 1-2 |
| Sodium hydroxy methylglicinate | 0.5-1.5 |
| Hydroxypropyl guar | 0.4-1.2 |
| Benzophenone-4 | 0.15-0.45 |
| Luviquat Polyquatenium 11 | 0.15-0.45 |
| Disodium EDTA dihydrate | 0.05-0.15 |
| Taurin | 0.03-0.08 |
| Calcium Pantothenate | 0.01-0.03 |
| $N^1$-methylspermidine | 0.00275-0.00825 |
| Galeopsis tetrahit estratto secco | 0.0003-0.0009 |
| Biotin | 0.00075-0.0025 |
| Meditanox H-10 | 0.0001-0.0002 |
| Water to 100 mL | |

Example 9

Cream

| Ingredients | % w/w |
|---|---|
| Octyldodecanol | 11.5-15.5 |
| Cetyl stearyl alcohol | 8.5-11.,5 |
| Cetylic esters wax | 2.6-3.5 |
| Sorbitan monostearate | 1.7-2.3 |
| Polysorbate 60 | 1.3-1.7 |
| Benzyl alcohol | 0.9-1.2 |
| $N^1$-Methylspermidine | 0.0428-0.058 |
| Biotin | 0.0119-0.0161 |
| Water to 100 mL | |

Example N. 10

Tablets

| Ingredients | Amount (mg) |
|---|---|
| Methionine | 200-400 |
| Coated vitamin C | 50-150 |
| Microcrystalline cellulose | 40-160 |
| Vitis vinifera seeds dry extract | 30-90 |
| Hydroxypropyl-methylcellulose K100 | 20-70 |
| Zeaxanthin 5% | 20-70 |
| Vitamin E acetate 50% | 20-50 |
| Selenium yeast 2000 ppm | 20-40 |
| Zinc bisglycinate 28.2% | 10-40 |
| Colloidal silicium dioxide | 10-20 |
| Olea Europaea L. leaf dry extract | 5-15 |
| Calcium Pantothenate | 5-11 |
| Polyethylene glycol 6000 | 4-12 |
| Magnesium stearate | 4-12 |
| Polyvinylpirrolidone K30 | 3-10 |
| Galeopsis segetum dry extract | 0.1-20 |
| Copper bisglycinate 30% | 2-6 |
| Rutin | 1-4 |
| Vitamin B6 | 1-4 |
| Hyaluronic acid | 1-2 |
| Spermidine Trihydrochloride | 0.3-0.8 |
| Folic acid | 0.1-0.3 |
| Biotin | 0.03-0.08 |

Example 11

Tablets

| Ingredients | Amount (mg) |
|---|---|
| Microcrystalline cellulose | 40-160 |
| Hydroxypropyl-methylcellulose K100 | 20-70 |
| Vitamin E acetate 50% | 20-50 |
| Zinc bisglycinate 28.2% | 10-40 |
| Colloidal silicium dioxide | 10-20 |
| Polyethylene glycol 6000 | 4-12 |
| Magnesium stearate | 4-12 |
| Polyvinylpirrolidone K30 | 3-10 |
| Copper bisglycinate 30% | 2-6 |
| Vitamin B6 | 1-4 |
| Hyaluronic acid | 1-2 |
| Spermidine Trihydrochloride | 0.3-0.8 |
| Biotin | 0.03-0.08 |

Example 12

Tablets

| Ingredients | Amount (mg) |
|---|---|
| Microcrystalline cellulose | 40-160 |
| Hydroxypropyl-methylcellulose K100 | 20-70 |

-continued

| Ingredients | Amount (mg) |
|---|---|
| Vitamin E acetate 50% | 20-50 |
| Zinc bisglycinate 28.2% | 10-40 |
| Colloidal silicium dioxide | 10-20 |
| Galeopsis segetum dry extract | 5-20 |
| Polyethylene glycol 6000 | 4-12 |
| Magnesium stearate | 4-12 |
| Polyvinylpirrolidone K30 | 3-10 |
| Copper bisglycinate 30% | 2-6 |
| Vitamin B6 | 1-4 |

Example 13

Materials and Methods

Immunoblot Analysis.

U2OS cells were grown to 80% confluence in Dulbecco Modified Eagle's Medium High Glucose (4.5 g/ID-Glucose) containing 4 mM L-glutamine, 10% fetal bovine serum (FBS) and treated with Spermidine (Lot. 2010112716), *Galeopsis segetum* (IDN 6781), Biotin (Lot. 2014124160) or their combinations. Protein samples were extracted in RIPA buffer as previously reported (De Mei C, Ercolani L, Parodi C, Veronesi M, Vecchio C L, Bottegoni G, et al. Dual inhibition of REV-ERBβ and autophagy as a novel pharmacological approach to induce cytotoxicity in cancer cells. *Oncogene.* 2015; 34(20):2597-608). p62/SQSTM1 and GAPDH levels were analyzed with anti-p62/SQSTM1 and anti-GADPH specific antibodies. Immunoblot experiments were performed in TBS-T buffer containing 5% bovine serum albumin (BSA). Anti-LC3B and anti-GAPDH antibodies were diluted 1:1000 and 1:50000, respectively. Complementary HPR-conjugated secondary antibodies were diluted 1:10000. Upon reaction with ECL Western blotting detection reagent, chemiluminescent signals were acquired with a LAS-4000 luminescent image analyzer and optical density of specific band signal was calculated with Photoshop image analysis software. GAPDH was adopted as a loading control and GAPDH signals were used to normalize p62 protein levels among different samples.

Immunoblots were repeated at least 4 times in order to express value as mean±SEM.

Fluorescent Analysis of Autophagy Inhibition.

U2OS cells were seeded 3000 cells/well in 48-well plates, No. 1.5 Uncoated Coverslip, 6 mm glass diameter, previously coated with gelatin solution, and transduced with 0.2 ul di baculovirus/10 000 cells containing a chimeric protein p62-Red Fluorescent Protein (p62-RFP). At 48 h post-transduction the cells were treated with Spermidine, Biotin, *Galeopsis*, or vehicle and monitored for 24 h using NIKON Live Cell Imaging microscopy.

Synergistic Activity of Spermidine, *G. segetum* and Biotin to Induce Autophagy in Human Cells In order to evaluate whether biotin and/or *Galeopsis segetum* extract may affect autophagy, the inventors monitored the accumulation of autophagosome in cultured U2OS cells by live fluorescent microscopy (Klionsky D J, Abdelmohsen K, Abe A, Abedin M J, Abeliovich H, Acevedo Arozena A, et al. Guidelines for the use and interpretation of assays for monitoring autophagy. Autophagy. 2016; 12(1): 1-222). Thus, cells were trasduced with construct containing the autophagy protein, LC3, fused with a Red Fluorescent Protein (RFP). Then, accumulation of fluorescent LC3 dots upon addition of biotin (200 ng/ml) or *Galeopsis* dry extract (100 ng/ml) was monitored by acquiring images every 30 min for 6 h. Spermidine (10 µM) was adopted as a positive control of an autophagy inducer compound (Pietrocola F, Lachkar S, Enot D, Niso-Santano M, Bravo-San Pedro J, Sica V, et al. Spermidine induces autophagy by inhibiting the acetyltransferase EP300. Cell Death & Differentiation. 2015; 22(3):509-16).

This analysis revealed a marked accumulation of fluorescent LC3 dots in both biotin- and *Galeopsis*-treated cells (see representative images in FIG. 1). As it is evident in FIG. 1 spermidine treatment resulted in a marked accumulation of LC3 fluorescent dots (i.e. accumulation of autophagosomes). Both biotin and *Galeopsis segetum* dry extract produced a similar accumulation of LC3-red dots.

Because LC3-RFP dots may also accumulate upon a blockade of the autophagic flux, the autophagy-dependent degradation of the SQSTM1/p62 protein (Klionsky D J, Abdelmohsen K, Abe A, Abedin M J, Abeliovich H, Acevedo Arozena A, et al. Guidelines for the use and interpretation of assays for monitoring autophagy. Autophagy. 2016; 12(1):1-222) was thus monitored. p62 served as a link between LC3 and ubiquitinated substrates (Pankiv S, Clausen T H, Lamark T, Brech A, Bruun J-A, Outzen H, et al. p62/SQSTM1 binds directly to Atg8/LC3 to facilitate degradation of ubiquitinated protein aggregates by autophagy. Journal of Biological Chemistry. 2007; 282(33): 24131-45). p62 and p62-bound polyubiquitinated proteins became incorporated into the completed autophagosome and were degraded in autolysosomes, thus serving as an index of autophagic degradation (Klionsky D J, Abdelmohsen K, Abe A, Abedin M J, Abeliovich H, Acevedo Arozena A, et al. Guidelines for the use and interpretation of assays for monitoring autophagy. Autophagy. 2016; 12(1):1-222).

Accordingly, the effects of biotin and *Galeopsis* on autophagy-mediated p62 degradation was evaluated analyzing the number of p62-RFP autophagosomes by live fluorescent microscopy. Cells were thus transduced with a construct expressing the p62 protein fused with the RFP. Then, p62 fluorescent dots were monitored upon addition of biotin, *Galeopsis*, spermidine or vehicle.

Figure 2:
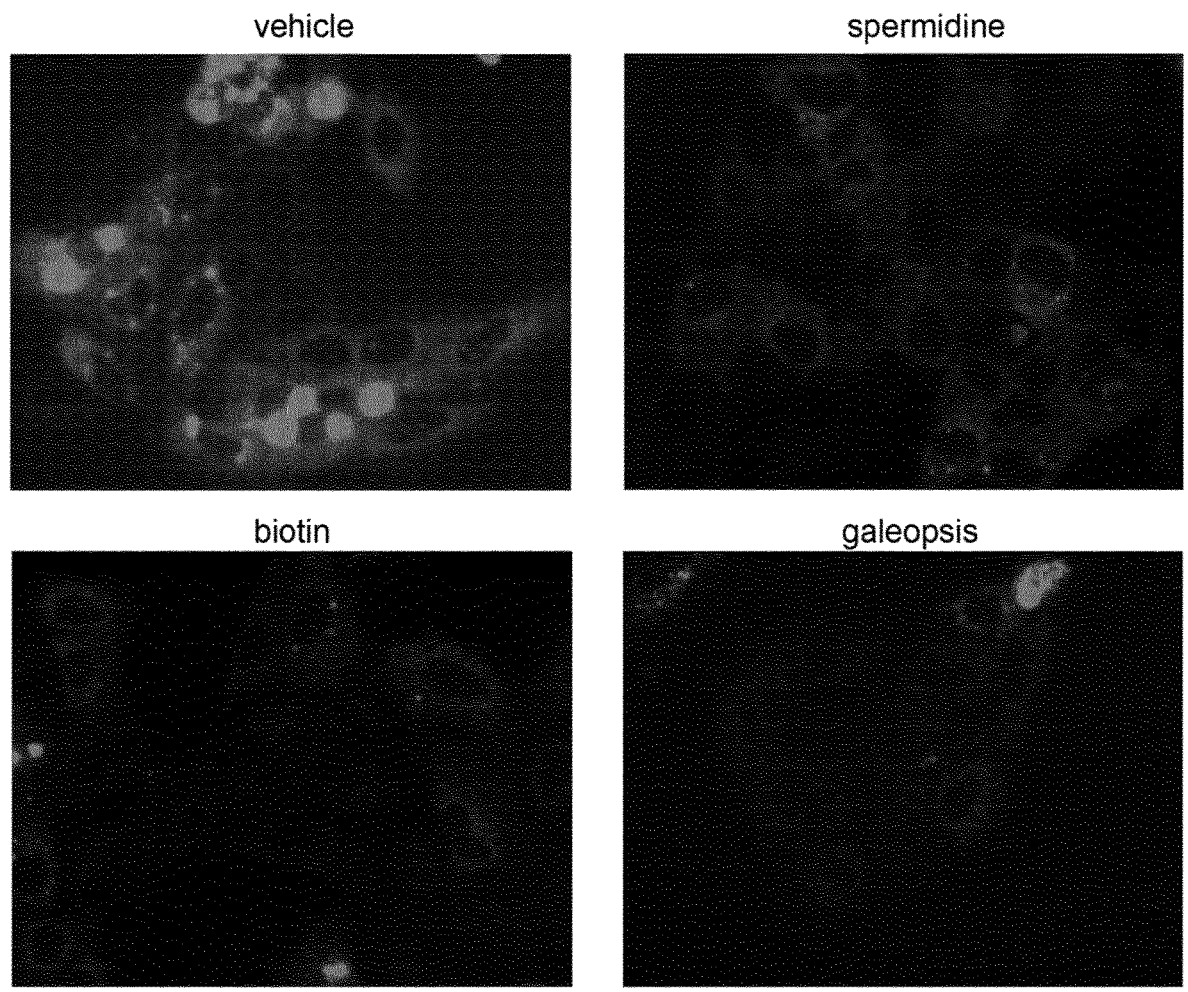
FIG. 2 shows representative images of U2OS cells transduced with a construct expressing the protein SQSTM1/p62 fused with a Red Fluorescent Protein (RFP) treated 6 hours with the indicated substances. SQSTM1/p62 turn-over mainly depends on the autophagy-mediated degradation process.

Fully supporting that both biotin and *Galeopsis* acted as autophagy inducers, a drastic reduction of p62-RFP dots was observed in treated cells compared with vehicle (see representative images in FIG. 2).

As seen in FIG. 2, the treatment with the previously characterized autophagy inducer, spermidine, markedly reduced p62 fluorescent dots and fluorescent signals, thus indicating that both biotin and *Galeopsis segetum* extract act as autophagy inducers, these treatments produced a strong reduction of p62 fluorescent signals.

Once validated the autophagy inducing activity of biotin and *Galeopsis*, and having validated the use of p62 as a suitable marker of the autophagy process, the effects of combinations of compounds on p62 protein levels by immunoblot analysis with specific anti-p62 antibodies were evaluated (De Mei C, Ercolani L, Parodi C, Veronesi M, Vecchio C L, Bottegoni G, et al. Dual inhibition of REV-ERBβ and autophagy as a novel pharmacological approach to induce cytotoxicity in cancer cells. Oncogene. 2015; 34(20):2597-608).

This analysis indicated a significant synergistic effects among spermidine, biotin and *Galeopsis* in inducing autophagy-mediated degradation of p62 (Table 1).

TABLE 1

| Treatment | Percentage of p62 reduction versus vehicle (% ± SEM) | Expected p62 reduction from additive effects | Synergistic effects |
|---|---|---|---|
| Spermidine | 5 ± 0.11 | | |
| Biotin | 21 ± 1.5 | | |
| Galeopsis | 24 ± 2.1 | | |
| Spermidine + Biotin | 45 ± 2.5 | 26 ± 1.61 | YES |
| Spermidine + Galeopsis | 51 ± 3.3 | 29 ± 2.21 | YES |
| Biotin + Galeopsis | 67 ± 5.5 | 45 ± 3.6 | YES |
| Spermidine + Galeopsis + Biotin | 78 ± 3.9 | 50 ± 3.71 | YES |

Indeed, the combination of spermidine (0.5 µM) and biotin (19.91 ng/ml) resulted in a p62 reduction almost twice bigger than the reduction expected by additive effects (45% vs 26%). Similar results were obtained for the combination of spermidine and *Galeopsis* (7.9 ng/ml) (51% VS 29%) and biotin/*Galeopsis* mix (67% vs 45%). Finally, a combination of all three compounds (0.5 µM spermidine+7.9 ng/ml *Galeopsis*+19.91 ng/ml biotin) generated an remarkable 78% reduction of p62 protein levels.

Example 14

Figures 3A, 3B:
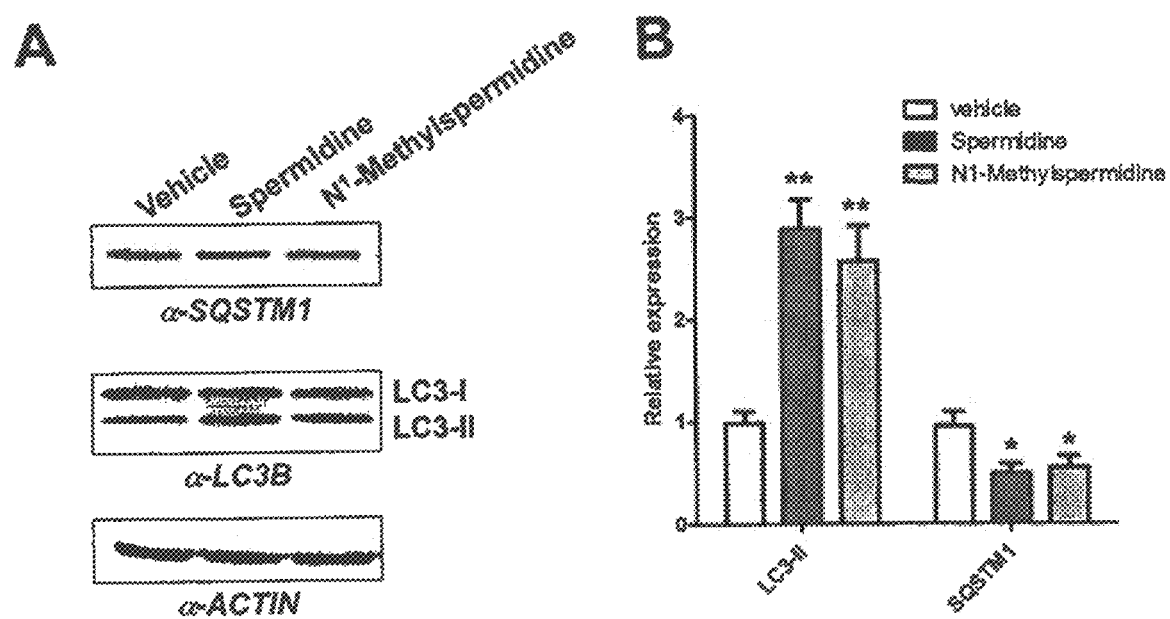
FIGS. 3A and 3B show the levels of lipidated LC3 and SQSTM1 in human U2OS cells treated with equimolar doses of N1-methylspermidine and spermidine as reported in Example 14.

The levels of lipidated LC3 and SQSTM1 in human U2OS cells treated with equimolar doses of N1-methylspermidine and spermidine were evaluated. As a result, compared with vehicle both compounds increased the levels of the lipidated LC3-II form and stimulated autophagy-mediated degradation of SQSTM1. Specifically cultured human U2OS cells were treated 6 h with vehicle or equimolar doses of spermidine and $N^1$-methylspermidine (100 µM). The levels of lipidated LC3 (LC3-II) and SQSTM1 were then assessed by immunoblotting analysis as in example 8 with specific antibody. Actin signals were adopted as a loading control. Densitometry analysis of protein signals is reported as relative protein levels normalized by ACTIN. Vehicle sample value was set to 1. Shown as mean±SEM., n=3. *$P<0.05$ and **$P<0.01$, compounds versus vehicle. The results are reported in FIG. 3 (A and B) These results validate that the $N^1$-methylspermidine retains the activity to induce autophagy, as its des-methylated analog.

The invention claimed is:

1. A synergistic composition for inducing autophagy in cells of human scalp hair follicles, stimulating hair growth, and treating or preventing hair loss, wherein the synergistic composition comprises an extract of plant of genus *Galeopsis* in the amount of 0.0003%-0.01% by weight and a compound promoting autophagy selected from R—$N^1$-spermidine or a salt thereof, wherein R is hydrogen or methyl in the amount of 0.0005-0.1%, biotin in the amount of 0.0006%-0.075% by weight, and mixtures thereof.

2. The synergistic composition of claim 1, wherein the extract of plant of genus *Galeopsis* is selected from the species of *Galeopsis segetum* and *Galeopsis tetrahit* and mixtures thereof.

3. The synergistic composition of claim 1, comprising an excipient comprising a maltodextrin and/or colloidal anhydrous silica gel.

4. The synergistic composition of claim 1, further comprising spermidine in the form of trihydrochloride.

* * * * *